(12) United States Patent
Wang (10) Patent No.: US 7,451,764 B2
(45) Date of Patent: Nov. 18, 2008

(54) NASAL MASK

(75) Inventor: Dave Wang, Room 4, 2F, No. 20, Daguan Rd., Sindian City, Taipei County (TW)

(73) Assignees: Dave Wang, Taipei County (TW); Angela Lu, Taipei County (TW)

( * ) Notice: Subject to any disclaimer, the term of this patent is extended or adjusted under 35 U.S.C. 154(b) by 0 days.

(21) Appl. No.: 10/832,389

(22) Filed: Apr. 27, 2004

(65) Prior Publication Data

US 2004/0211425 A1    Oct. 28, 2004

(30) Foreign Application Priority Data

| | | | |
|---|---|---|---|
| Apr. 28, 2003 | (TW) | ............................. | 92109936 A |
| Aug. 12, 2003 | (TW) | ............................. | 92122044 A |
| Apr. 5, 2004 | (TW) | ............................. | 93109359 A |

(51) Int. Cl.
- *A61B 19/00* (2006.01)
- *A61M 16/00* (2006.01)
- *A62B 7/10* (2006.01)
- *A62B 18/08* (2006.01)
- *A62B 18/02* (2006.01)

(52) U.S. Cl. ............. 128/206.18; 128/863; 128/200.26; 128/201.26; 128/206.12; 128/206.17; 128/207.13; 128/206.11

(58) Field of Classification Search ............ 128/204.11, 128/204.12, 204.13, 204.14, 206.11, 207.18, 128/203.12, 201.25, 200.24, 205.27, 205.29, 128/206.14, 206.16, 848, 858, 206.17, 206.18, 128/206.19; 606/199, 204.45

See application file for complete search history.

(56) References Cited

U.S. PATENT DOCUMENTS

| | | | | |
|---|---|---|---|---|
| 3,921,636 | A * | 11/1975 | Zaffaroni | 424/432 |
| 4,030,491 | A * | 6/1977 | Mattila | 128/206.11 |
| 4,221,217 | A * | 9/1980 | Amezcua | 128/206.11 |
| 4,267,831 | A * | 5/1981 | Aguilar | 128/203.14 |
| 4,327,719 | A * | 5/1982 | Childers | 128/206.11 |
| 5,425,359 | A * | 6/1995 | Liou | 128/206.11 |
| 5,922,006 | A * | 7/1999 | Sugerman | 606/204.45 |
| 5,931,852 | A * | 8/1999 | Brennan | 606/199 |
| 6,015,425 | A * | 1/2000 | Altadonna, Jr. | 606/204.45 |
| 6,386,197 | B1 * | 5/2002 | Miller | 128/206.11 |

(Continued)

FOREIGN PATENT DOCUMENTS

CN    2155240    2/1994

(Continued)

*Primary Examiner*—Justine R. Yu
*Assistant Examiner*—Annette F Dixon
(74) *Attorney, Agent, or Firm*—Bacon & Thomas, PLLC (57) ABSTRACT

A nasal mask comprising a pair of main bodies, which respectively form a containing space having an open end and a through-hole end; a connection which connects the edges of the opening ends of the main bodies; and a filtration device disposed inside the containing space of the main bodies. An alar projection is disposed at the upper brim of the opening end of the main bodies, which seals with the superior alar nasi of the nasal cavity. The main bodies forms a structure sealed with the nasal cavity. The main bodies of the nasal mask is made of soft elastic material and seals with the nasal cavity through the arrangement of an alar projection at the upper margin of the opening end of said main bodies that provides the wearer a sense of comfort.

15 Claims, 6 Drawing Sheets

U.S. PATENT DOCUMENTS

| | | | |
|---|---|---|---|
| 2003/0106556 A1* | 6/2003 | Alperovich et al. | 128/206.11 |
| 2004/0089303 A1* | 5/2004 | Chien | 128/206.11 |
| 2005/0061325 A1* | 3/2005 | Michaels | 128/206.11 |

FOREIGN PATENT DOCUMENTS

| | | |
|---|---|---|
| CN | 2208951 Y | 10/1995 |
| DE | 20200168 U1 | 5/2002 |
| GB | 2354952 | 4/2001 |
| JP | 11342214 | 12/1999 |
| TW | 469833 | 12/2001 |
| TW | 326693 | 2/2008 |

* cited by examiner

NASAL MASK

BACKGROUND OF THE INVENTION

1. Field of the Invention

The present invention provides a nasal mask, particularly a nasal mask having the function of air filtering, controlled release of medication, or an ergonomic nasal mask, or a multi-functional nasal mask that can filter air, control release of medication, and offer ergonomic comfort.

2. Description of the Related Art

The emission of exhausts from motorcycles, cars, factories, power plants, and waste treatment plants and dusts around cement factories and construction sites have made air pollution an increasingly serious problem. Many city dwellers choose to wear mask when they go out to keep off filthy particles in the air. Traditional masks cover both the nose and the mouth, making its wear inconvenient to the user. In addressing this problem, a prior art disclosed in Taiwan Patent No.469833 relates to an insertion-type nasal filter which consists of a main body having two activated carbon pieces; said main body has a pair of large-diameter sleeve insert connected by a horizontal strip, and said pair of sleeve insert respectively has an entry hole. The main body of aforesaid nasal mask is made of soft material and may be fitted into nasal cavity of different sizes to closely engage the walls of nostril. The two activated carbon pieces are adhered to air inhalation hole to filter air passing through into the nasal passages.

Another prior art as illustrated in Taiwan Patent No.326693 discloses a nasal insert with filtering effect comprising two nasal cannula and two activated carbon filters, wherein said nasal cannula has a unitarily connected netted base and a unitarily connected netted cap with a space retainer formed in between for placement of activated carbon filters. A flexible connecting piece is arranged between the two nasal cannula which can be secured on the bridge of nose. The cylindrical activated carbon filters are mounted in the space retainer with the netted cap closed before the cannulas are inserted into the nostril. The connecting member between the cannula is secured on the bridge of nose and the two cannula are secured inside the nostrils without slip-off.

The insertion-type nasal masks of the prior art represent an improvement of conventional mask, but both the nasal mask and nasal cannula have smooth surface design such that the smooth surface is unable to form a seal with the nasal cavity and the insert tends to slip off. Their filtering effect also comes into question. The prior art could filter particulates in the air and activate the air, but the use of activated carbon filter only does not provide therapeutic or health effect, hence restricting the functions of the nasal mask.

To address the drawbacks of prior art that use only activated carbon filter and tend to slip off due to the inability to form a seal with the nasal cavity, the present invention provides a nasal mask having the multiple functions of air filtering, controlled release of medication and ergonomic construction. Said nasal mask, through the design of main body that conforms to the internal walls of the nasal cavity, securely engages the nasal cavity that does not slip easily and is more comfortable to wear than smooth-surfaced nasal mask or nasal cannula disclosed in the prior art. By placing filter material having bactericidal, bacteriostatic or controlled medication release effect in the filtration device disposed in the main body, the nasal mask can be worn for health or therapeutic purpose. The nasal mask of the present invention can also be connected with a medical appliance, such as oxygen tube or other medical instrument to provide more advanced treatment. The nasal mask provided herein can also be used in animals with a nasal construction to prevent the transmission of infectious disease among animals or for treatment.

SUMMARY OF THE INVENTION

The object of the present invention is to provide a nasal mask having air filtering function, which, by placing a filtration device in the main body of the mask, can achieve bactericidal and/or bacteriostatic effects.

Another object of the present invention is to provide a nasal mask having the function of controlled release of medication, which, by placing a filtration device loaded with foamed microcapsule containing medication, can slowly release the medication for direct absorption by nasal mucosa so as to achieve health or therapeutic effect.

Yet another object of the present invention is to provide an ergonomic nasal mask, in which, through the arrangement of an alar projection at the upper margin of the opening end of the mask's main body, the main body of the mask forms a seal with the nasal cavity to provide comfort to the user.

A further object of the present invention is to provide a multi-functional nasal mask having the functions of air filtering, controlled release of medication and ergonomic comfort, wherein the use of an detachment prevention means having uneven construction increases the seal of the mask with intranasal structure, and the use of filtering material having bactericidal, bacteriostatic or controlled medication release effects in the filtration device achieves health or therapeutic effects.

The nasal mask according to the present invention comprises a pair of main bodies which respectively form a containing space having an opening end and a through-hole end;
  a connecting member used for connecting the edges of the opening ends of said pair of main bodies; and
  a filtration device disposed inside the containing space of each one of said main bodies;
  characterized in that: an alar projection is disposed at the upper brim of the opening end of each one of said main bodies, which seals with the superior alar nasi of a nasal cavity and said main bodies forms a structure sealed with the nasal cavity; the said main bodies of the nasal mask is made of soft elastic material.

The said main bodies of the nasal mask can further include one or a plurality of detachment prevention means.

The detachment prevention may be a recess for engaging the brim of nostril formed between said opening end and alar projection.

The detachment prevention means may be a septal cartilage plug disposed at the upper rim of main body's through-hole end.

The detachment prevention means may be an alar trough formed along the rim of main body's through-hole end in the shape of a curved arc.

The detachment prevention means may be an alar notch disposed at the outer rim of alar projection.

The connecting member may be a holder to engage the septal cartilage; said holder may be in the curved arc shape, U-shape or C-shape.

Said flexible soft material may be silicon rubber, thermoplastic polyurethane (TPU), thermoplastic rubber (TPR), or polymer having hydroscopic property.

The containing space of said main bodies is further arranged with a plurality of grooves on its side wall.

The filtration device may be filter material.

The filtration device may be a disposable filter or unitarily formed filter.

Said filter material may have netted construction.

Said filter material may be woven or non-woven fabric material.

Said filter material may be foam material having filtering effect.

Said filter material may be foam or non-woven fabric having microcapsules allowing controlled release of medication.

The nasal mask of the present invention in another embodiment comprises a pair of main bodies, said main bodies respectively form a containing space having an opening end and a through-hole end;
 a connecting member for connecting the edges of the opening ends of said pair of main bodies;
 a filtration device disposed inside the containing space of each one of said main bodies; and
 a pair of adjustable nostril membranes disposed at the brim of the opening end of each one of said main bodies;
 characterized in that: an alar projection is disposed at the upper brim of the opening end of each one of said main bodies, which seals with the superior alar nasi of nasal cavity; said main bodies closely engages the nasal cavity; the main bodies of the nasal mask is made of soft elastic material, while said adjustable nasal membrane extends from the brim of the opening end of said main bodies to seal with the front end of nostril.

The main body of nasal mask can further include a clip-on device.

Said clip-on device may be an outer rim sleeve clip for securing fabric containing bioactive agent to be absorbed directly by the nasal mucosa.

Said adjustable nostril membrane may be in flared shape, wherein said membrane forms a plurality of tearable lines along which the size of opening end may be adjusted to fit the nostril.

DETAILED DESCRIPTION OF THE INVENTION

Figure 1:
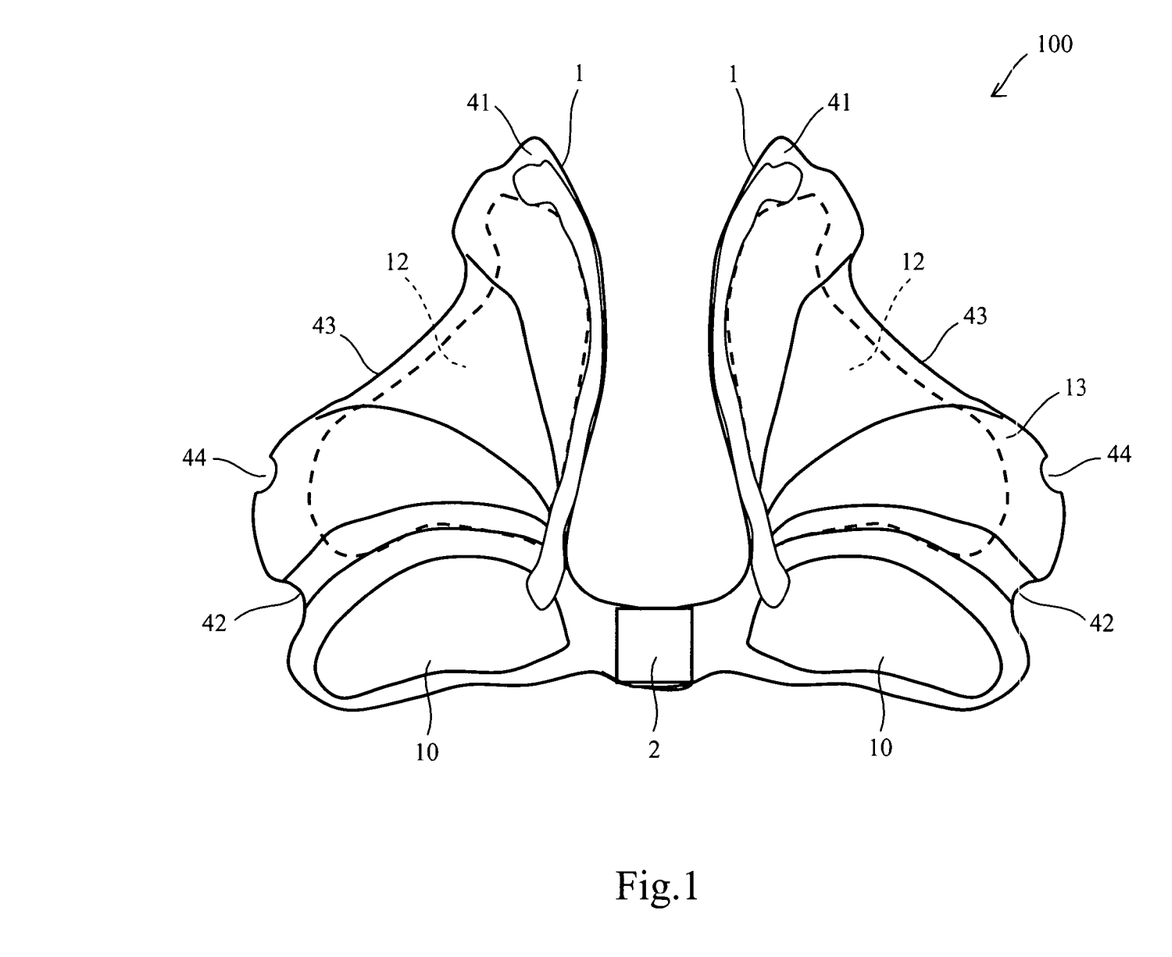
FIG. 1 shows the front side view of nasal mask constructed according to the invention.

As shown in FIG. 1 depicting the front side view of nasal mask according to the present invention, the nasal mask 100 comprises a pair of main bodies 1 which respectively forms a containing space 12 having an opening end 10 and a through-hole end 11 (see FIG. 2); a connecting member 2 for connecting the edges of opening end 10 of pair of main bodies 1; and a filtration device 3 (see FIG. 2) disposed in the containing space 12 of said main body 1.

Figure 2:
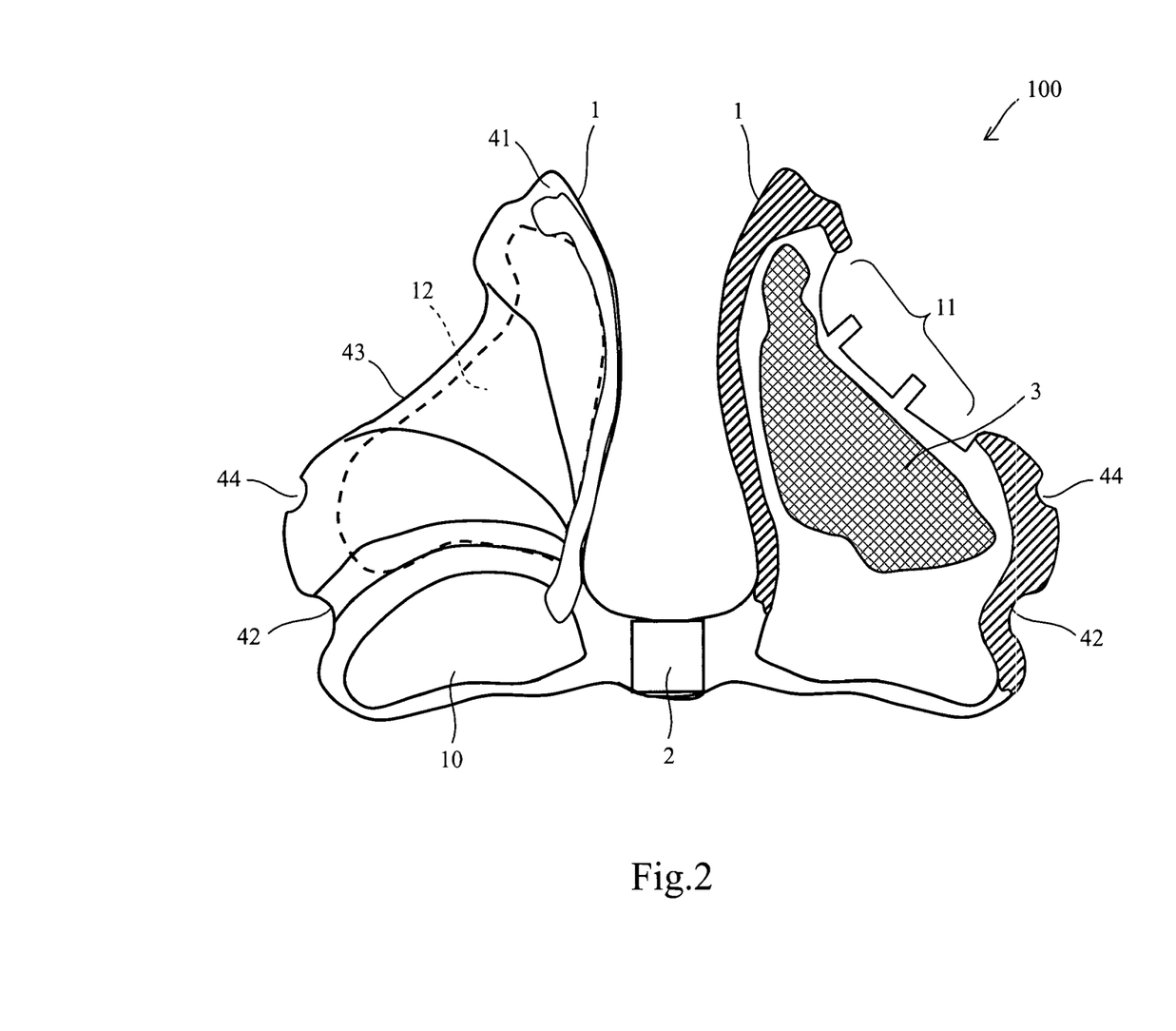
FIG. 2 shows the sectional view of main body of nasal mask according to the invention.

Referring to FIG. 1 and FIG. 2 which depicts the sectional view of main body of nasal mask, an alar projection 13 is disposed at the upper brim of opening end 10 of said main body 1 which is configured and shaped to seal with interior surface contours of a superior margin of a nasal alar so the main body 1 closely engages within a nostril. The connecting member 2 is a holder in curved arc shape, which engages the septal cartilage of nose when the nasal mask 100 is worn. The filtration device 3 is bactericidal and/or bacteriostatic filter material in netted construction, which is a disposable filter designed separately from main body 1 and can be replaced or repeatedly used. The main body 1 and connecting member 2 are made of soft elastic material thermoplastic polyurethane (TPU).

In this embodiment, the main body 1 of nasal mask is further disposed with an detachment prevention means in the form of a septal cartilage plug 41 formed at the upper rim of through-hole end 11 of main body 1 to engage against the septal cartilage in the nostril so as to increase the seal of nasal mask 100 within the nostril to keep it from dislodging.

In a preferred embodiment of the invention, the main body 1 of nasal mask is further disposed with a plurality of detachment prevention means, including a recess 42 for engaging the brim of a nostril disposed between opening end 10 and alar projection 13; a septal cartilage plug 41 disposed along the upper rim of through-hole end 11 of main body 1; an alar trough 43 formed (i.e., configured and shaped) along the rim of through-hole end 11 of main body 1 into a curved arc; and an alar notch 44 disposed at the outer rim of alar projection 13.

When wearing the nasal mask 100, a filter material is first placed into the containing space 12 of main body 1 from the opening end 10 before the nasal mask is placed into the nostrils of a user. Due to the alar projection 13 disposed at the upper brim of opening end 10 and the septal cartilage plug 41 disposed at the upper rim of through-hole end 11 of main body 1, the main body 1 seals with interior surface contours of the nostrils so it will not slip or dislodge from the nostrils.

Figure 3:
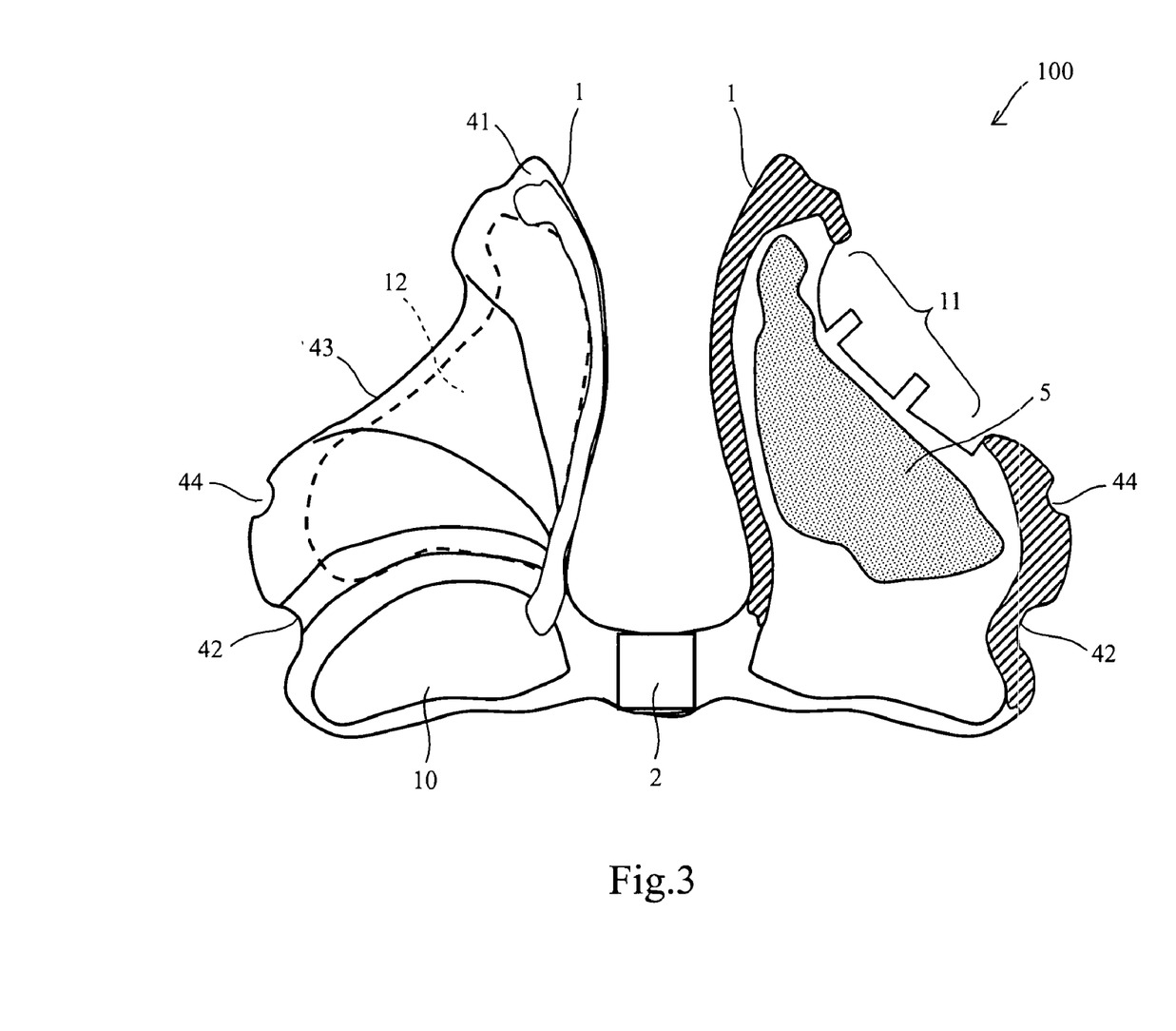
FIG. 3 shows the sectional view of main body of nasal mask according to another embodiment of the invention.

Referring to FIG. 3 which illustrates the sectional view of main body portion of another embodiment, the filter material for the filtration device therein is foamed microcapsule 5 having controlled release effect which allows slow release of bioactive material for direct absorption by nasal mucosa to achieve health and/or therapeutic effect. The other structures of this embodiment are the same as those described above.

Figure 4:
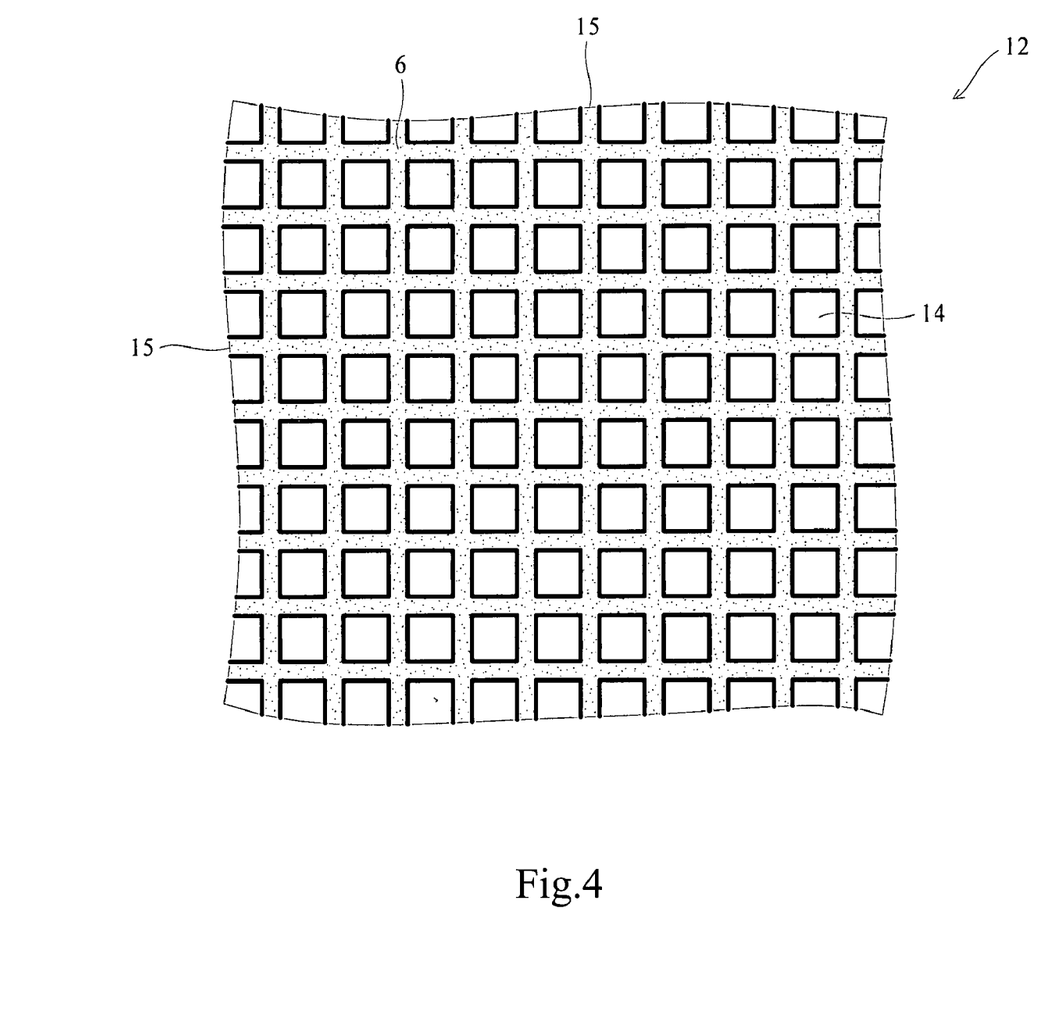
FIG. 4 shows the schematic diagram of the side wall groves of nasal mask according to another embodiment of the invention.

Referring to FIG. 4 which shows another example of filtration device for the nasal mask, the filtration device of nasal mask 100 consists of grooves 15 carved on side wall 14 inside containing space 12 of main body 1, where timed release medication 6 is adhered to the grooves 15 and absorbed directly by the respiratory tract and nasal mucosa of user when the nasal mask is worn to achieve health and/or therapeutic effects.

Figure 5:
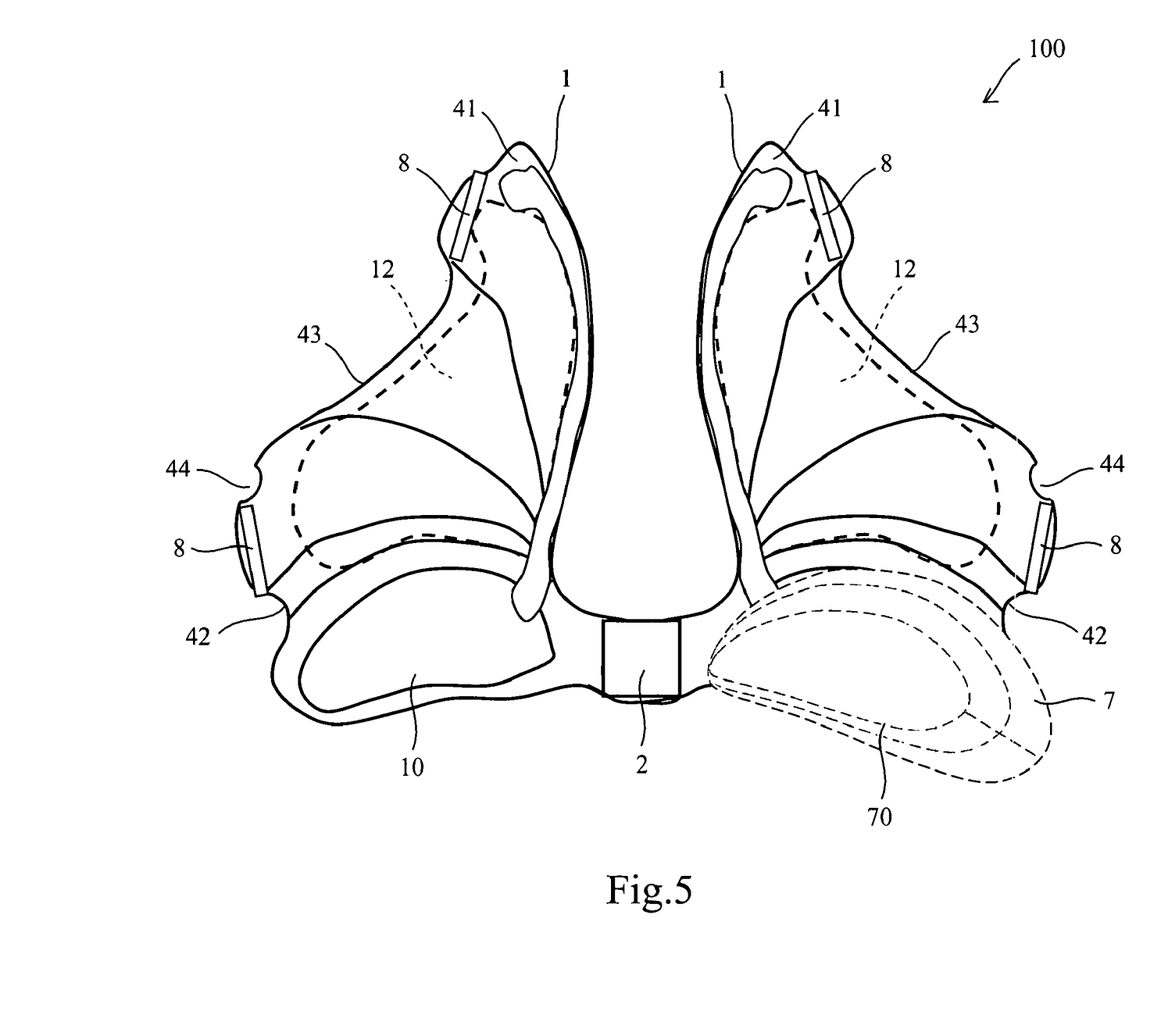
FIG. 5 shows the front side view of nasal mask according to another embodiment of the invention.
Figure 6:
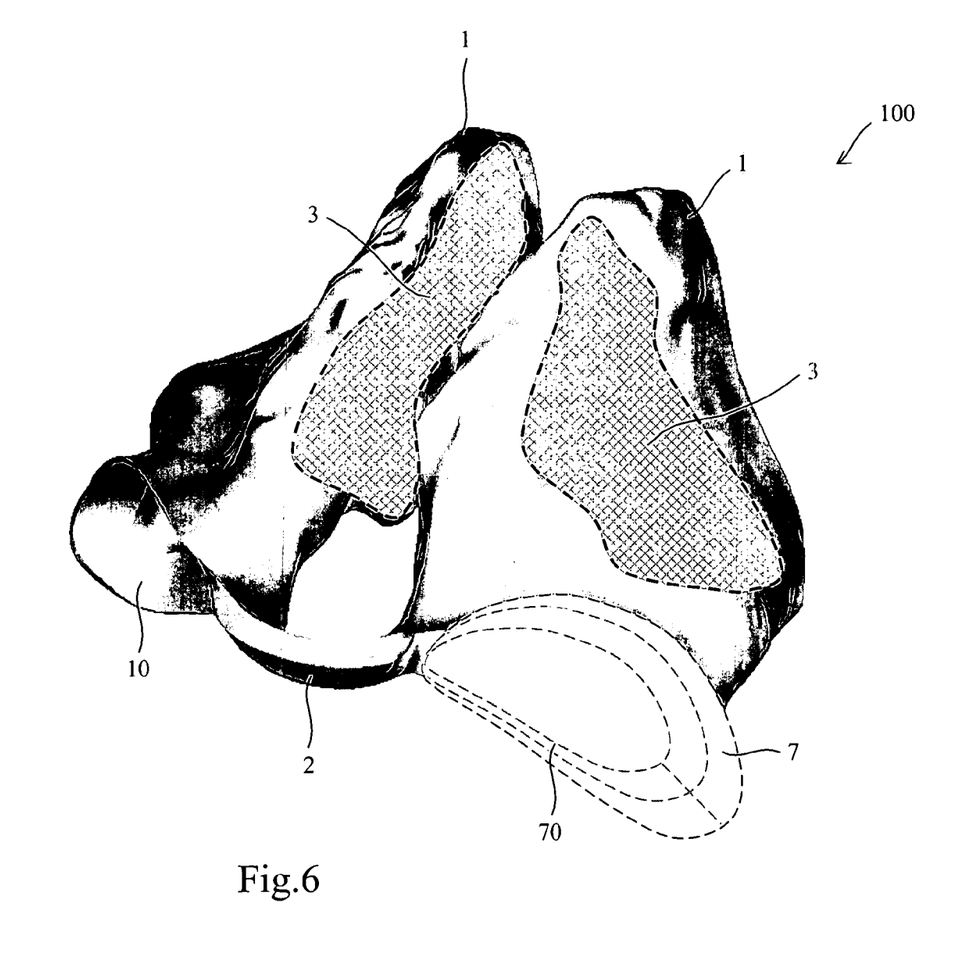
FIG. 6 shows the schematic diagram of adjustable nostril membrane according to another embodiment of the invention.

Referring to FIGS. 5, 6 and 2, another embodiment of nasal mask of the invention shows that the nasal mask 100 comprises a pair of main bodies 1, which forms respectively a containing space 12 having an opening end 10 and through-hole end 11; a connecting member 2 for connecting the edges of opening ends 10 of pair of main bodies 1; a filtration device disposed in the containing space 12 of main body 1; and a pair of adjustable nostril membranes 7 disposed at the brim of the opening end 10 of main body 1; and a clip-on device, which is preferably an outer rim sleeve clip 8 disposed at the side of cartilage fitting member 41 and the side of alar projection 13 to secure fabric containing bioactive agent for direct absorption by nasal mucosa.

Again referring to FIG. 5 and 6, an alar projection 13 is disposed at the upper brim of opening end 10 of nasal mask 1 which seals with interior surface contours of the superior margin of a nasal alar so the main body 1 closely engages the nostril. The connecting member 2 is a holder in curved arc shape, which engages the septal cartilage of nose when the nasal mask 100 is worn. The filtration device 3 is bactericidal and/or bacteriostatic filter material in netted construction, which is a disposable filter designed separately from main body 1 and can be replaced or repeatedly used. The main body 1 and connecting member 2 are made of soft elastic material TPU. The adjustable nostril membrane 7 is in flared shape having a plurality of tearable lines 70 when the user of the nasal mask has larger nostril that there is gap between the main body 1 of nasal mask and the user's nostril, the hole size of opening end may be adjusted by tearing along the lines to let the mask fit the nasal cavity of the user better.

In this embodiment, the main body 1 of nasal mask is further disposed with an detachment prevention means in the form of a septal cartilage plug 41 disposed along the upper rim of through-hole end 11 of main body 1 to engage the cartilages inside the nostril so as to increase the seal of nasal mask 100 with the interior the nostril to keep it from disengaging.

The preferred embodiments of the present invention have been disclosed in the examples. However the example should not be construed as a limitation on the actual applicable scope of the invention, and as such, all modifications and alterations without departing from the spirits of the invention and appended claims shall remain within the protected scope and claims of the invention.

What is claimed is:

1. A nasal mask, comprising:
   a pair of main bodies each having an open outer end, an open inner end, and a through-hole that extends from the outer end to the inner end and forms a containing space, wherein each main body is configured for insertion into a nostril of a user's nose with the inner end disposed at a position further within the nostril than the outer end;
   a connecting member for connecting edges of the opening ends of said pair of main bodies;
   each of the main bodies having a septal cartilage plug, the septal cartilage plug being an upward-protruding ridge extending generally from the outer end proximate to said connecting member toward the inner end;
   each of the main bodies having an alar projection disposed at an upper brim of the outer end, the alar projection being a convex projection formed on a surface of the main body and separated from said septal cartilage ridge by an alar trough;
   each of the main bodies having an alar notch formed in the alar projection;
   wherein the alar projection is adapted to seal with the inside of a nasal ala and the septal cartilage plug is adapted to engage septal cartilage when the main bodies are inserted into said user's nostrils.

2. The nasal mask according to claim 1, wherein said connecting member is made of soft elastic material.

3. The nasal mask according to claim 2, wherein said connecting member has a U-shape, C-shape or curved arc shape whereby the connecting member is adapted to engage the septal cartilage of a nose when the nasal mask is worn.

4. The nasal mask according to claim 1, wherein said soft elastic material is silicon rubber, thermoplastic polyurethane (TPU), thermoplastic rubber (TPR), or polymer having hydroscopic property.

5. The nasal mask according to claim 1, wherein the containing space of said pair of main bodies further has a plurality of grooves disposed on its side wall.

6. The nasal mask according to claim 1, wherein said filtration device is a filter material.

7. The nasal mask according to claim 6, wherein said filter material has netted construction.

8. The nasal mask according to claim 6, wherein said filter material is a woven or non-woven fabric.

9. The nasal mask according to claim 6, wherein said filter material is a foam having filtering effect.

10. The nasal mask according to claim 6, wherein said filter material is a foam or a non-woven fabric having microcapsules allowing controlled release of medication.

11. A nasal mask, comprising:
    a pair of main bodies each being closely engageable with the inside of a nostril, said main bodies respectively forming a containing space having a flare-shaped open outer end, an open inner end and a through-hole that extends from the outer end to the inner end and forms said containing space, and an alar projection disposed at an upper brim of the outer end, wherein the alar projection seals with a nasal ala of the nostril;
    a connecting member for connecting the edges of the opening ends of said pair of main bodies;
    a filtration device disposed inside the containing space of each one of said main bodies; and
    a pair of flare-shaped nostril membranes each correspondingly disposed at a brim of the flare-shaped opening end of one of said main bodies, said flare-shaped nasal membranes extending from the brim of the flare-shaped opening ends of said main bodies to seal with the front end of a nostril;
    each of the main bodies having an alar projection disposed at an upper brim of the outer end, and an alar notch formed on said alar projection; wherein the alar projection is adapted to seal with the inside of the nasal ala when the main bodies are inserted into user's nostrils.

12. The nasal mask according to claim 11, wherein said nasal mask further comprises a clip-on device.

13. The nasal mask according to claim 12, wherein said clip-on device is an outer rim sleeve clip.

14. The nasal mask according to claim 13, wherein said outer rim sleeve clip has curved arc shaped.

15. A nasal mask, comprising:
    a pair of main bodies each being closely engageable with the inside of a nostril, said main bodies respectively forming a containing space having a flare-shaped opening end and a through-hole end and an alar projection disposed at an upper brim of the flare-shaped opening end, wherein the alar projection seals with an alar of the nostril;
    a connecting member for connecting the edges of the opening ends of said pair of main bodies;
    a filtration device disposed inside the containing space of each one of said main bodies; and
    a pair of flare-shaped nostril membranes each correspondingly disposed at a brim of the flare-shaped opening end of one of said main bodies, said flare-shaped nasal membranes extending from the brim of the flare-shaped opening ends of said main bodies to seal with the front end of a nostril;
    wherein said flare-shaped nostril membrane comprises at least one tearable line where the size of the opening end is adjusted by tearing along said tearable line.

* * * * *